United States Patent
Scherl

(10) Patent No.: US 7,140,059 B2
(45) Date of Patent: Nov. 28, 2006

(54) RANDOM ORBITAL TOOTHBRUSH

(75) Inventor: Dale Scherl, Lawrence, KS (US)

(73) Assignee: Colgate-Palmolive Company, New York, NY (US)

(*) Notice: Subject to any disclaimer, the term of this patent is extended or adjusted under 35 U.S.C. 154(b) by 100 days.

(21) Appl. No.: 11/115,426

(22) Filed: Apr. 27, 2005

(65) Prior Publication Data

US 2005/0188483 A1    Sep. 1, 2005

Related U.S. Application Data

(63) Continuation of application No. PCT/US2003/34587, filed on Oct. 30, 2003.

(60) Provisional application No. 60/422,706, filed on Oct. 31, 2002.

(51) Int. Cl.
*A61C 17/22* (2006.01)

(52) U.S. Cl. .......................... 15/22.1; 15/28

(58) Field of Classification Search ............. 15/22.1, 15/28
See application file for complete search history.

(56) References Cited

U.S. PATENT DOCUMENTS

| 864,201 | A | 8/1907 | Shers |
|---|---|---|---|
| 1,577,751 | A | 3/1926 | Paschall |
| 1,981,688 | A * | 11/1934 | Conti ............... 15/28 |
| 1,997,352 | A * | 4/1935 | Fleet ............... 15/22.1 |
| 2,140,307 | A | 12/1938 | Belaschk et al. |
| 4,027,348 | A | 6/1977 | Flowers et al. |
| 4,102,084 | A | 7/1978 | Bloomquist |
| 4,175,299 | A | 11/1979 | Teague, Jr. et al. |
| 4,177,535 | A | 12/1979 | Cole |
| 4,276,672 | A | 7/1981 | Teague, Jr. et al. |
| 4,336,622 | A | 6/1982 | Teague, Jr. et al. |
| 4,854,085 | A | 8/1989 | Huber |
| 5,504,959 | A | 4/1996 | Yukawa et al. |
| 5,687,442 | A | 11/1997 | McLain |

FOREIGN PATENT DOCUMENTS

| DE | 4243220 | * | 6/1994 |
| DE | 4318976 | * | 12/1994 |

* cited by examiner

Primary Examiner—Mark Spisich
(74) Attorney, Agent, or Firm—Ellen K. Park

(57) ABSTRACT

A toothbrush includes a support member mounted on a first shaft in the head of the toothbrush. A carrier member is mounted on a second shaft to the support member. The support member is eccentrically mounted so that when its first shaft is rotated the carrier member is moved in an orbital path during the rotation of the support member. The carrier member is freely mounted on its second shaft so that during this orbital movement the carrier member rotates in a random manner. Cleaning elements such as bristles extend outwardly from the carrier member.

21 Claims, 1 Drawing Sheet

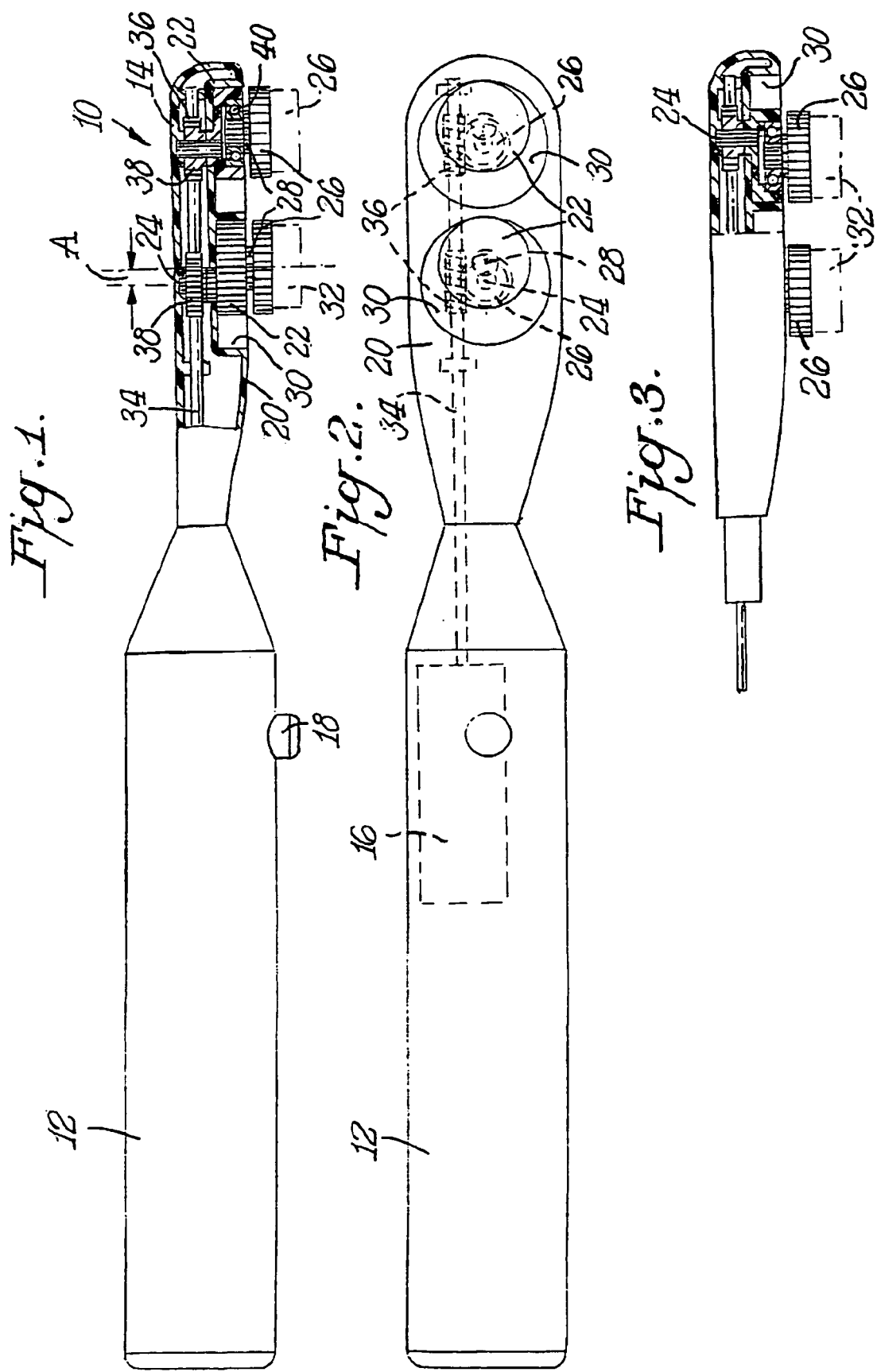

RANDOM ORBITAL TOOTHBRUSH

This application is a continuation of application PCT/US2003/34587, filed Oct. 30, 2003, which claims the benefit of U.S. Provisional Application 60/422,706 filed Oct. 31, 2002, both of which are incorporated herein by reference in their entirety.

BACKGROUND OF THE INVENTION

Various attempts have been made to provide toothbrushes with cleaning elements such as bristles movably mounted to enhance the cleaning action. U.S. Pat. No. 5,504,959 discloses an electric toothbrush having circular brush bases which engage rotating bases. The rotating bases move linearly while they are rotating. The brush head itself is capable of rotating about its axis during these movements. U.S. Pat. Nos. 4,175,299, 4,276,672 and 4,336,622 all relate to toothbrushes which are characterized as having an orbital brush action. During operation the brush head moves in contact with the teeth and then in its return stroke is angled out of contact with the teeth. As a result of this orbital motion the brush by being retracted does not contact the teeth and gums or at least lessens the pressure during the return stroke. U.S. Pat. No. 6,347,425 discloses a powered toothbrush having three dimensional rotational head movement.

It would be desirable if a toothbrush could be provided having enhanced rotational movements which differs from the type of movements disclosed in the above patents.

SUMMARY OF THE INVENTION

An object of this invention is to provide a toothbrush wherein the cleaning elements, such as the bristles, move in a random orbital path.

A further object of this invention is to provide such a toothbrush which is electrically powered to cause the random orbital path movement.

In accordance with this invention the head of a toothbrush includes at least one carrier member from which the cleaning elements extend outwardly. The carrier member is mounted to the front face of the head in such a manner that the carrier member and the cleaning elements move in a random orbital path.

In a preferred practice of the invention the carrier member is mounted to a support member. The support member is eccentrically mounted on a shaft so that when the support member rotates the carrier member moves in an orbital path. The carrier member itself is freely mounted for rotation with respect to the support member so that the carrier member rotates in a random fashion while it is moving through the orbital path.

THE DRAWINGS

FIG. 1 is a side elevational view partly in section of a toothbrush in accordance with this invention;

FIG. 2 is a front elevational view of the toothbrush shown in FIG. 1; and FIG. 3 is a side elevational view partly in section of the toothbrush shown in FIGS. 1–2 in a different phase of operation.

DETAILED DESCRIPTION

The present invention is in general directed to an electric toothbrush with a head that orbits in a random manner so as to remove more plaque and debris with less effort. By moving in such a path the toothbrush should be move efficient at removal of plaque and debris than a standard orbit head of an electric toothbrush.

FIGS. 1–3 illustrate a toothbrush 10 in accordance with this invention. As shown therein the toothbrush 10 includes a hollow handle 12 and a head 14. Handle 12 would house the power drive for the toothbrush. This could include, for example, a motor 16 controlled by switch 18. Actuation of the motor which is part of a drive structure causes later described drive transmitting members to effect a random orbital motion in the head 14. More particularly, head 14 has a front face 20 which includes a support member 22 rotationally mounted on a first shaft 24. As illustrated support member 22 is eccentrically mounted on shaft 24. A carrier member 26 is mounted on a second shaft 28 to support member 22. Second shaft 28 is displaced from first shaft 24 by the distance "A". As a result, when support member 22 is rotated on its first shaft 24 carrier member 26 is driven in an orbital path. Front face 20 includes a recessed receiving area 30 which defines the limits of that orbital path.

As best illustrated in FIGS. 1 and 3 support member 22 is mounted below the outer surface of face 20 in the recess 30. Carrier member 26, however, extends outwardly from the outer surface of face 20. Carrier 26 is provided with cleaning elements 32 extending outwardly from the outer face of carrier member 26. Carrier member 26 is freely mounted on its second shaft 28. As a result, when carrier member 26 is driven in its orbital path carrier member 26 also freely or randomly rotates about its own shaft 28. In the illustrated embodiment carrier member 26 is axially mounted on shaft 28. If desired, however, carrier member 26 could be eccentrically mounted so as to increase the random orbital path that carrier member 26 and its cleaning elements 32 take. In the preferred illustrated practice of this invention carrier member 26 is a disk having a circular outer surface from which the cleaning elements 32 extend.

During operation of toothbrush 10 the carrier members 26 and their cleaning elements 32 would move in the orbital path which is transcribed by the outer wall of recess 30. Thus, FIGS. 1 and 2 show the carrier members 26 in one position located furthest from the handle 12. FIG. 3 shows the carrier members moved to the opposite end of the path where the carrier members are closest to handle 12.

The invention could be practiced with a single carrier member and a single support member. As illustrated, however, a pair of such carrier members 26,26 and support members 22,22 is provided. The invention can also be practiced where there are more than two sets of carrier members and support members.

The drawings illustrate the cleaning elements 32 in a schematic manner. Any suitable cleaning elements may be used such as bristles or elastomeric members including massage elements.

Any suitable drive structure can be utilized for creating the random orbital path. Such type of path, for example, is known from random-orbital sanders. Reference is made to U.S. Pat. No. 4,120,084, all of the details of which are incorporated herein by reference thereto. The '084 patent describes a type of drive structure that could be adapted for creating the random orbital path of the cleaning elements 32. Such structure, in general, includes a drive shaft 34 which would be driven by motor 16. Drive shaft 34 rotates in a longitudinal direction. A worm gear 36 is mounted at spaced locations on shaft 34 in accordance with the number of sets of carrier members and support members. Worm gear 36 drives gear 38 (see FIG. 1) which in turn drives first shaft 24. Second shaft 28 is displaced from first shaft 24 by the distance A. As a result, during the driven rotation of support member 22, carrier member 26 moves in an orbital path. Second shaft 28 may be mounted in roller bearings 40 as described in the '084 patent.

Although reference has been made to U.S. Pat. No. 4,102,084 for an exemplary type of drive mechanism other types of drive mechanisms may also be used such as known for random-orbit sanders. Reference is also made to U.S. Pat. No. 4,854,085.

In general, a drive mechanism would be used wherein the drive structure includes a motor, preferably located in the handle of the toothbrush. The motor actuates drive transmitting members which cause a first shaft to rotate. A support member which could be in the form of a disk or block is eccentrically mounted on the first shaft. A second shaft is mounted to the outer surface of the support member. A carrier member which is preferably a disk is freely mounted on the second shaft. Thus, when the drive structure is actuated the support member is directly driven by the drive structure which creates an orbital path. Because the carrier member is freely rotatably mounted on the support member the carrier member would rotate in a random fashion while being moved in the orbital path.

What is claimed is:

1. A random orbital toothbrush comprising a handle, a head secured to one end of said handle, said head having a front face, at least one carrier member having outwardly extending cleaning elements, and a drive structure mounting said carrier member to said front face for moving said carrier member and said cleaning elements in a random orbital path, wherein said at least one carrier member is a disk mounted to a support member, said support member being eccentrically mounted to a first shaft, said drive structure being engaged with said first shaft to rotate said first shaft, a second shaft mounted to said support member offset from said first shaft, and said disk being mounted to said second shaft.

2. The toothbrush of claim 1 wherein said disk is freely mounted to said second shaft.

3. The toothbrush of claim 2 wherein said cleaning elements are bristles.

4. The toothbrush of claim 3 wherein said disk has a circular outer face from which said bristles extend.

5. The toothbrush of claim 1 including a plurality of carrier members mounted to a plurality of support members.

6. A random orbital toothbrush comprising a handle, a head secured to one end of said handle, said head having a front face, at least one carrier member having outwardly extending cleaning elements, and a drive structure mounting said carrier member to said front face for moving said carrier member and said cleaning elements in a random orbital path, wherein at least one said carrier member is mounted to a support member, said support member being eccentrically mounted to a first shaft, said drive structure being engaged with said first shaft to rotate said first shaft, a second shaft mounted to said support member offset from said first shaft, and said carrier member being mounted to said second shaft.

7. The toothbrush of claim 6 wherein, said support member being mounted to said front face, said carrier member being movable with respect to said support member, and said support member being movable with respect to said front face.

8. The toothbrush of claim 7 wherein each of said carrier member and said support member is rotatably movable.

9. The toothbrush of claim 8 wherein said support member is mounted to said front face for rotational movement in an orbital path.

10. The toothbrush of claim 9 wherein said support member is drivably mounted for movement in said orbital path.

11. The toothbrush of claim 7 including a plurality of said carrier members and said support members.

12. The toothbrush of claim 6 wherein said cleaning elements are bristles.

13. The toothbrush of claim 6 wherein said carrier member is a disk having a circularly shaped outer surface from which said cleaning elements extend.

14. The toothbrush of claim 6 wherein said handle is hollow, said drive structure is mounted in said handle and includes a drive transmitting member which extends from said handle and into said head.

15. The toothbrush of claim 6 wherein said drive structure includes a motor and a drive transmitting member driven by said motor and extending into said head.

16. A random orbital toothbrush comprising a handle, a head secured to one end of said handle, said head having a front face, at least one carrier member having outwardly extending cleaning elements, and a drive structure mounting said carrier member to said front face for moving said carrier member and said cleaning elements in a random orbital patH, wherein said drive structure includes a motor and a drive transmitting member driven by said motor and extending into said head;

wherein said carrier member is mounted to a support member, said support member being mounted to said front face, said carrier member being movable with respect to said support member, and said support member being movable with respect to said front face;

wherein each of said carrier member and said support member is rotatably movable;

wherein said support member is eccentrically mounted to a first shaft mounted to said front face for rotational movement in an orbital path;

wherein said support member is drivably mounted for movement in said orbital path; and wherein said carrier member is freely rotatably mounted on a second shaft mounted on said support member for random rotation.

17. The toothbrush of claim 16 wherein said carrier member is axially mounted on said second shaft.

18. The toothbrush of claim 16 wherein said carrier member is eccentrically mounted on said second shaft.

19. The toothbrush of claim 16 including a plurality of said carrier members and said support members.

20. The toothbrush of claim 16 wherein said cleaning elements are bristles.

21. The toothbrush of claim 16 wherein said carrier member is a disk having a circularly shaped outer surface from which said cleaning elements extend.

* * * * *